United States Patent [19]

Stavovy et al.

[11] 4,044,598

[45] Aug. 30, 1977

[54] PERFORMANCE EVALUATION FACILITY FOR SEAL SKIRT-FINGERS OF SURFACE EFFECT SHIPS

[75] Inventors: Alexander B. Stavovy, Springfield; Richard H. Chiu, Falls Church, both of Va.

[73] Assignee: The United States of America as represented by the Secretary of the Navy, Washington, D.C.

[21] Appl. No.: 710,946

[22] Filed: Aug. 2, 1976

[51] Int. Cl.² .................... G01N 3/56; G01M 10/00; B63B 9/00
[52] U.S. Cl. ....................................... 73/7; 73/432 SD
[58] Field of Search ................ 73/432 SD, 148, 88 R, 73/147, 7; 180/127; 33/397

[56] References Cited

U.S. PATENT DOCUMENTS

| | | | |
|---|---|---|---|
| 2,205,102 | 6/1940 | Loudenslager et al. | 73/88 R |
| 3,103,118 | 9/1963 | Friedman et al. | 73/88 R |
| 3,379,271 | 4/1968 | Hopkins et al. | 180/127 X |
| 3,739,634 | 6/1973 | Johnson et al. | 73/147 |
| 3,964,316 | 6/1976 | Abe | 73/432 SD |

*Primary Examiner*—Daniel M. Yasich
*Attorney, Agent, or Firm*—R. S. Sciascia; Q. E. Hodges

[57] ABSTRACT

A testing system and method for testing and evaluating the performance and service life of finger seals and skirts used on surface effects ships (SES). The system simulates actual conditions that SES seals would encounter and tests full scale portions of seals and skirts. The system and method comprises placing a number of seals together in a mounting frame that moves the finger relative to another surface to simulate the chaffing and wear that occurs during actual pitch and roll. Below and in contact with the finger seals/skirts is a surface which has a wave-shaped rigid contoured surface movable as a unit vertically and horizontally. On the surface is a water-retaining pile-like material that retains water flowed thereon.

10 Claims, 1 Drawing Figure

U.S. Patent    Aug. 30, 1977    4,044,598
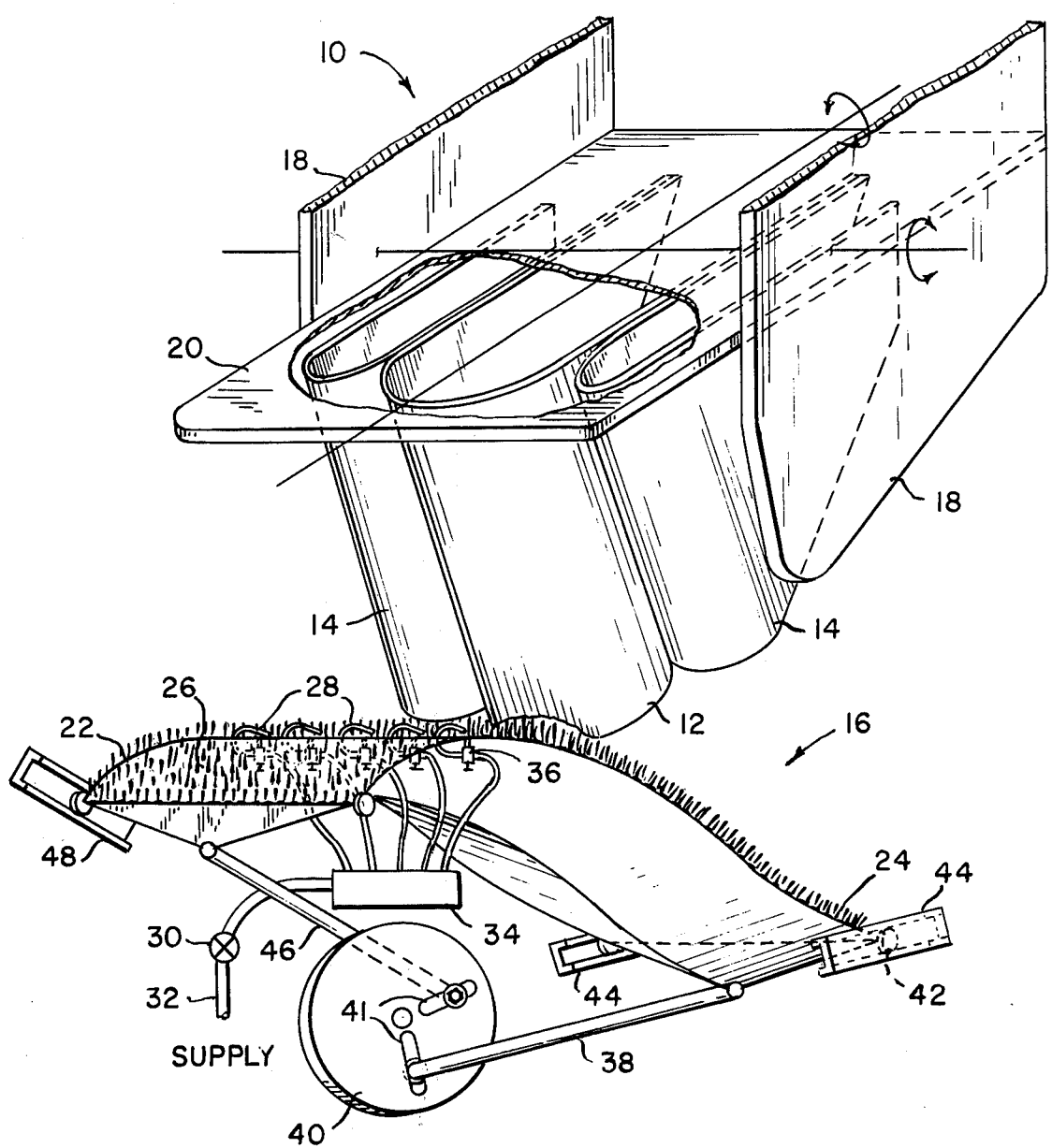

PERFORMANCE EVALUATION FACILITY FOR SEAL SKIRT-FINGERS OF SURFACE EFFECT SHIPS

The invention described herein may be manufactured and used by or for the Government of the United States of America for governmental purposes without the payment of any royalties thereon or therefor.

BACKGROUND OF THE INVENTION

This invention relates to a performance evaluation facility and more particularly to a system which simulates actual operating conditions on surface effect ship's finger seals and skirts of full-scale size.

Generally in the past, the methods used for evaluation of SES finger seal/skirts were to expose the seal material itself to abrading surfaces to evaluate service life or endurance. The finger structure (only a component of the whole skirt) was subjected to clubs or water-jets which beat on the finger structure's surface. These methods were done on small scale material samples and structures, were not statistically accurate, and obviously were not a realistic representation of actual surface loads and forces which the full-scale seal/skirts would later experience in service. Because of the material composition, and the complex geometries and characteristics of the seal structures, the small-scale data couldn't be extrapolated with statistical confidence. Observation of a 100 ton surface effects vehicle performance showed that the small-scale tests did not correlate to the actual seal wear and deformation produced in actual operation. Experience on the craft has shown that seal deterioration is directly affected by interface boundary forces and direct impact on the finger and bag structure. Thus it is concluded that the prior art methods are inadequate in representing actual and real service conditions and service life performance evaluation of seal structures.

SUMMARY OF THE INVENTION

Briefly the instant invention overcomes the disadvantages of the prior art surface effects ship seal performance testing methods by providing a facility and method which simulates actual operating conditions on surface effect seals on a full scale basis to determine deterioration. The test set-up incorporates a full size finger portion of a skirt flanked by two other full scale fingers to simulate interface boundary conditions. All three of these fingers are mounted in a test frame which moves to simulate controllable roll, pitch, and bag stiffness. A wave profile is simulated by a rigid contoured surface, movable vertically and horizontally, and has flowing water over a water retaining surface.

STATEMENT OF THE OBJECTS OF THE INVENTION

Accordingly, an object of the invention is to provide a new, improved, efficient and reliable performance evaluation facility for surface effect ship seal skirts and fingers.

Another object of the instant invention is to provide a surface effect ship seal performance test and evaluation facility that simulates actual conditions that the seals would encounter while the ship is underway.

Still another object of the present invention is to provide a surface effect ship seal performance evaluation facility that simulates full-scale interface boundary conditions including pitch and roll as well as wave conditions.

BRIEF DESCRIPTION OF THE DRAWINGS

A more complete understanding of the invention and many of the attendant advantages thereto will be apparent from the following detailed description when considered in conjunction with the accompanying drawings, wherein the FIGURE is an isometric view partially in section, showing a portion of a seal skirt-finger in a performance evaluation facility according to the invention.

DESCRIPTION AND OPERATION OF THE PREFERRED EMBODIMENT

Referring now to the drawings there is shown in the figure generally an evaluation facility comprising a mounting frame 10. The frame holds a test finger 12, in the form of an internally pressurized cylindrical membrane, with boundary condition simulation fingers 14 of similar shape on either side of the finger 12 and also against the frame 10. Below the mounting finger and frame assembly, is a contoured wave surface 16.

Referring particularly to the mounting frame 10, it comprises two parallel and vertical side plates 18, constraining the boundary condition simulation fingers 14 to press against the test finger 12. Fixed between the side plates 18 is a horizontal plate 20 laying on top of the open fingers 12, 14 thereby constraining them to simulate bag pressure stiffness. The mounting frame 10 carrying the fingers 12, 14 has two degrees of freedom, that is, it can rotate about one axis to simulate roll, and rotate about another axis to simulate pitch as shown in the drawing by the double ended arcuate arrows drawn about the axes drawn on the plate 20, one of said axes passing through side plates 18.

Below the mounting frame 10 and fingers 12 and 14 is the contoured wave surface 16 that is a rigid material such as aluminum, steel, plastic or the like, thicker along the center of the waveform than along the edges for rigidity. The contoured wave surface 16 may be in the form of a sine wave having a crest end 22 and a trough end 24.

Affixed on the top of the wave surface 16 as with an adhesive or the like, is a flexible, water retaining material 26 with a deep pile, having upstanding parallel fibers having wear resistance, secured to a backing, such as a cut-pile rug, "Astro-Turf", or the like. This material 26 when wetted will retain water to be slippery to simulate an actual wave. The material is wetted with water from a plurality of waterjets 28 at the crest end 22 directing the flow toward the trough end 24. The waterjets are controllable in exit speed by a control valve 30 in a supply line 32 from a source of water. For simplicity the supply line connects to a manifold 34 to which all the waterjets 28 are connected. The waterjets are also controllable, as to their position in relation to the pile of the water retaining material, by a screw arrangement 36. The position may be above or within the pile. The rate of flow and position controllability can simulate the effect of wave celerity and penetration depth on the test finger at a predetermined test speed.

The contoured wave surface 16 is movable both horizontally and vertically to simulate wave height or amplitude and speed of travel. A horizontal movement linkage 38, which may be adjustable in length, is pivotally connected to the trough end 24 of the wave surface 16 and to rotary drive 40, which may take the form of a crank or wheel having radial slots 41 to provide for variable stroke reciprocating movement.

The trough end 24 has small wheels 42 rotatably mounted thereon that ride in tracks 44 to guide the contoured wave surface in a linear horizontal direction. Also pivotally connected to the rotary drive 40, in a slot 41 to provide for variable stroke and which may be varied as to speed, is a vertical movement linkage 46, which may be adjustable in length. The other end of the vertical movement linkage 46 is pivotally connected to crest end 24 of the wave surface 16. The crest end also has small wheels 42 rotatably mounted thereon that ride in tracks 48 (one shown) to guide the contoured wave surface in a linear vertical direction.

In operation, the seal test finger 12 of the prototype size, shape, and material is placed in the mounting frame 10 of the evaluation facility between two boundary condition simulation fingers 14. The mounting frame 10 is then lowered to place the bottom of the fingers 14, 16 into contact with the contoured wave surface 16.

The test is started by rotating the mounting frame about a horizontal transverse axis to control pitch simulation, and about a horizontal longitudinal axis to control roll simulation. These provide the effect of surface effect ship simulated conditions on the test finger such as would actually be encountered under operating conditions.

The contoured wave surface 16 is then set into action by rotating the rotary drive 40 which starts both horizontal and vertical wave motion. At the same time, the water flow to the waterjets 28 is adjusted by opening the valve 30. The depth of the waterjets is adjusted by the screw arrangement 36 to provide a flow through the pile water retaining surface to best simulate the waves that the test finger might actually encounter.

Thus a surface effect ship seal skirt-finger performance evaluation facility is provided that can test the effect of actual conditions on a prototype finger on a full-scale, size, shape, and material basis. The seal structures can then be evaluated under this realistic simulation of the actual service conditions with statistical accuracy at moderate fabrication and operating costs. Otherwise, an alternative method would be to test finger in a wave-making model basin.

Obviously, many modifications and variations of the present invention are possible in light of the above teachings. It is therefore to be understood that within the scope of the appended claims, the invention may be practiced otherwise than as specifically described.

What is claimed is:

1. A system for testing seal skirt fingers of surface effect ships comprising:
   a sample skirt finger;
   a first means for moving sample skirt finger to simulate both pitch and roll motion of an actual skirt finger on a surface effect ship underway;
   an adjustable second means producing a flow of water over said finger's surface to simulate the effect of waterflow on said finger when said finger is mounted on a surface effect ship underway;
   a third means for simulating an ocean wave profile and operatively connected to said second means for contacting and flexing said finger to simulate movement of said finger when underway, whereby the wear of said finger under service conditions may be determined.

2. The testing system of claim 1 wherein said first means is further defined by:
   a fourth means for supporting said test finger at its top and for moving it in the pitch and roll motion.

3. The testing system of claim 2 wherein said fourth means furthercomprise:
   a fifth means including the sample shirt finger for simulating the effect of adjacent fingers when said finger is mounted on a ship.

4. The testing system of claim 3 wherein said fifth means includes
   a pair of parallel, vertical side plates;
   a pair of boundary condition simulating fingers mounted between said side plates, contacting and pressing on the test finger for simulating the action of adjacent fingers; and
   a horizontal plate between said side plates and resting on top of the fingers for simulating bag pressure stiffness for said test finger.

5. The testing system of claim 2 wherein said fourth means is controlled in amplitude and rate.

6. The testing system of claim 1 wherein said second means includes:
   a rigid contoured surface having a crest and a trough, said surface being movable vertically and horizontally for simulating wave amplitude and speed.

7. The testing system of claim 6 wherein said second means further includes:
   a plurality of waterjets maintaining the flow of water over the top of said contoured surface; and
   a water retention surface affixed to said contoured surface over and through which the water flows.

8. The testing system of claim 7 wherein said water retention surface comprises:
   a pile material having upstanding parallel fibers.

9. A Method for testing a sample of a full-scale seal skirt-fingers of a surface effect ships comprising the steps of:
   mounting a test finger sample in a test mechanism and moving the test skirt-finger sample by the mechanism to simulate the movement imparted to the finger by pitch and roll movement of a surface effect ship underway;
   mounting the sample finger between two contacting fingers to simulte the effect of adjacent fingers on the test skirt-finger; and
   applying a coating of water to a selected one of said fingers and a surface of said simulating mechanism;
   applying a wave like motion to a contoured surface which contacts the test skirt finger to simulate the effect of wave action on the test skirt-finger whereby the effect of ship motion on the skirt-fingers may be evaluated.

10. The method for testing of claim 9 wherein the step of simulating wave action further comprises the steps of:
    moving said contoured wave surface vertically and horizontally both controllable in speed and amplitude to simulate various wave heights and speeds; and
    flowing water over said contoured wave surface to simulate an actual water wave celerity and friction.

* * * * *